US00PP25088P3

(12) United States Plant Patent
Korlipara

(10) Patent No.: US PP25,088 P3
(45) Date of Patent: Nov. 18, 2014

(54) *ECHINACEA* PLANT NAMED 'METEOR PINK'

(50) Latin Name: ***Echinacea* hybrid**
Varietal Denomination: Meteor Pink

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 125 days.

(21) Appl. No.: 13/815,536

(22) Filed: Mar. 8, 2013

(65) Prior Publication Data

US 2014/0259244 P1 Sep. 11, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

*Primary Examiner* — June Hwu
(74) *Attorney, Agent, or Firm* — Klarquist Sparkman, LLP

(57) ABSTRACT

A new and distinct *Echinacea* plant named 'Meteor Pink' characterized by enlarged disc florets forming an anemone-type inflorescence, light pink ray florets and medium pink disc florets, ray florets which are held horizontally, a short, mounding habit with excellent stem count, and excellent vigor.

1 Drawing Sheet

Botanical denomination: *Echinacea* hybrid.
Variety designation: 'Meteor Pink'.

BACKGROUND OF THE INVENTION

The present invention relates to a new and distinct cultivar of *Echinacea* and given the cultivar name 'Meteor Pink'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids of *Echinacea paradoxa*×*Echinacea purpurea*.

Compared to *Echinacea* 'Secret Romance' (U.S. Plant Pat. No. 23,036), the new cultivar is shorter and has inflorescences with contrasting bright pink disc florets and light pink ray florets rather than all medium pink.

Compared to *Echinacea* 'Pink Double Delight' (U.S. Plant Pat. No. 18,803), the new cultivar is shorter, has more crowns, and a more upright habit, with larger inflorescences that are a different shade of pink.

This new *Echinacea* cultivar is distinguished by:

1. enlarged disc florets forming an anemone-type inflorescence,
2. light pink ray florets and medium pink disc florets,
3. ray florets which are held horizontally,
4. a short, mounding habit with excellent stem count, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Echinacea* 'Meteor Pink' growing in the trial field in full sun in early July in Canby, Oreg.

DETAILED PLANT DESCRIPTION

The following is a detailed description of the new *Echinacea* cultivar based on observations of two-year-old specimens growing in the trial beds in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.
*Hardiness.*—USDA Zones 4 to 9.
*Size.*—Grows to about 49 cm wide and 56 cm tall to top of inflorescences.
*Form.*—Basal clump, with about 18 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 5 inflorescences per stem.
*Size.*—To 51 cm tall to a terminal inflorescence and 8 mm wide at base.
*Internode length.*—1 cm to 9 cm.

*Surface texture.*—Strigose.
*Color.*—Yellow Green 146B.

Leaf (basal):
*Type.*—Simple.
*Shape.*—Ovate to lanceolate.
*Arrangement.*—Basal.
*Blade size.*—Grows to 14 cm long and 6 cm wide.
*Margins.*—Serrate.
*Apex.*—Acuminate.
*Base.*—Attenuate.
*Surface texture.*—Strigose on both sides.
*Venation.*—Pinnate, with 3 main veins from the base, Yellow Green 145D on both sides.
*Color.*—Topside, Green N137A, bottom side closest to Yellow Green 147B.
*Petiole description.*—Grows to 10 cm long and 5 mm wide above the clasp, sparsely strigose, Yellow Green 147C.

Leaf (stem):
*Type.*—Simple.
*Shape.*—Ovate to lanceolate.
*Arrangement.*—Alternate.
*Blade size.*—Grows to 16 cm long and 7 cm wide.
*Margins.*—Coarsely serrate to entire, slightly undulate.
*Apex.*—Acuminate.
*Base.*—Attenuate.
*Surface texture.*—Strigose on both sides.
*Venation.*—Pinnate, with 3 main veins from the base, Yellow Green 145D on both sides.
*Color.*—Topside Green 137B, bottom side closest to Yellow Green 147B.
*Petiole description.*—On all but upper leaves, clasping, grows to 4 cm long and 7 mm wide above the clasp, strigose, both sides Yellow Green 147B on sides and 147C in center.

Inflorescence:
*Type.*—Composite on terminal stalked heads.
*Number of flowering stems from the ground.*—About 40.
*Flowering stem.*—Grows to 51 cm tall from the base of the plant to the terminal inflorescence and can grow to 10 cm long from the top stem leaf to the base of an inflorescence; branched with 1 to 5 inflorescences per stem; diameter growing to 11 mm wide near the inflorescence; strigose; Yellow Green 146B.
*Size.*—Grows to 9 cm wide and 8 cm deep as disc enlarges.
*Form.*—Ray florets held slightly reflexed, mature disc is conic.
*Immature inflorescence.*—Grows to 2.5 cm wide and 2.1 cm deep, ray florets held at a 40 degree angle from the horizontal and rolled up so only the back color shows, Yellow Green 150D, disc color Green N137A.
*Ray florets.*—Without pistil or stamen, about 28 in number, grow to 52 mm long and 10 mm wide, oblanceolate with the tip three-toothed (teeth to 5 mm long and 2.5 mm wide), tips acute, entire margins, base attenuate, glabrous on both sides; top side Red Purple 73C, bottom side Greyed Purple 186D.
*Disc.*—Flat becoming conic, growing to 33 mm deep and 50 mm wide with maturity, Yellow Green 144A in the background and Yellow Orange 17A in the foreground when disc florets are closed to Red Purple 64A when disc florets are open.
*Disc florets.*—To about 400 in number, each with 1 pistil and 4 stamen, grow to 16 mm long and 5 mm wide, each with one persistent, very stiff linear bract (15 mm long with tip Greyed Purple 187A then 3 mm Orange 17B blending to 5 mm Yellow Green 145D to White 155A at base); corollas to 12 mm long and 5 mm wide, tubular at base (to 8 mm long and 2 mm wide, Yellow Green 145A on back side and Red Purple 61B on topside, fan 5 mm wide and 5 mm deep, 5 to 6 lobed, lobes lanceolate, reflexed, to 6 mm long and 1 mm wide, margin entire, tips acute, base attenuate, glabrous on both sides, topside Red Purple 61A, bottom side Red Purple 61B; pistil 12 mm long, ovary 3.5 mm long, White NN155A, style 5 mm long White 155A, 2-branched stigma spreading, Greyed Purple 187A; stamen 4 mm long, filaments 1.5 mm long, threadlike, White 155A, anthers 2.5 mm long, Brown 200C, pollen Yellow Orange 15A.
*Phyllaries.*—In 4 leafy series, area grows to 40 mm wide and 10 mm deep, lobes lanceolate in shape, reflexed, grow to 12 mm long and 4 mm wide, both sides Yellow Green 147B, margins strigose, tip acute, strigose.
*Receptacle.*—Grows to 15 mm wide and 18 mm deep, White 155B.
*Bloom period.*—July through October in Canby, Oreg.
*Fragrance.*—Sweet, floral.
*Lastingness.*—Each inflorescence lasts about three weeks in Canby, Oreg.

Seeds: None seen.
Fertility: Poor.
Disease and pests: No pests or diseases have been observed on plants grown under commercial conditions in Canby, Oreg. No resistances are known.

I claim:

1. A new and distinct *Echinacea* plant as herein illustrated and described.

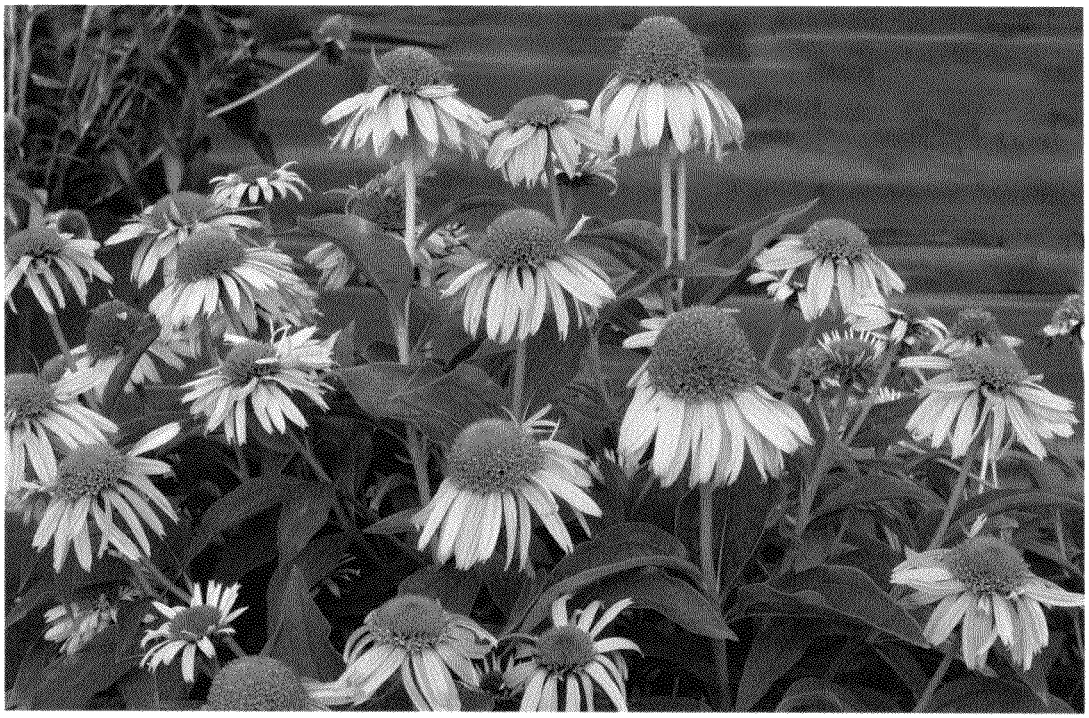

* * * * *